US00PP10431P

United States Patent [19]

Meewisse

[11] Patent Number: Plant 10,431

[45] Date of Patent: Jun. 2, 1998

[54] GUZMANIA PLANT NAMED 'LAMBADA'

[75] Inventor: Johannes S. M. Meewisse, Erica, Netherlands

[73] Assignee: H.A. Meewisse B.V., Erica, Netherlands

[21] Appl. No.: 780,699

[22] Filed: Jan. 8, 1997

[51] Int. Cl.[6] ..... A01H 5/00

[52] U.S. Cl. ..... Plt./88.8

[58] Field of Search ..... Plt./88.8

*Primary Examiner*—James R. Feyrer
*Assistant Examiner*—Kent L. Bell
*Attorney, Agent, or Firm*—C. A. Whealy

[57] ABSTRACT

A distinct cultivar of Guzmania plant named 'Lambada', characterized by its tall and broad growth habit; arching broad leaves; branched inflorescenes with showy bright red floral bracts and bright yellow sepals; and tolerance to wet media.

3 Drawing Sheets

The present invention relates to a new and distinct cultivar of Guzmania plant, botanically known as Guzmania, and hereinafter referred to by the cultivar name 'Lambada'.

The new cultivar was discovered in 1989 by the inventor in Erica, The Netherlands, in a controlled environment as a naturally occurring mutation in a large population of plants of the non-patented cultivar 'Festival'. The new cultivar was identified as a single plant within this population of plants of the cultivar 'Festival'.

Asexual propagation of the new cultivar at Erica, The Netherlands, has shown that the unique features of this new Guzmania plant are stable and reproduced true to type in successive generations of asexual propagation.

The following traits have been repeatedly observed and are determined to be the unique characteristics of 'Lambada'. These characteristics in combination distinguish 'Lambada' as a new and distinct cultivar:

1. Tall and broad growth habit.
2. Arching broad leaves.
3. Branched inflorescences with showy bright red floral bracts and bright yellow sepals.
4. Tolerance to wet media.

Plants of the new Guzmania differ from plants of the present cultivar, 'Festival', in the following characteristics:

1. Plants of the new Guzmania are taller and broader than plants of the cultivar 'Festival'.
2. Leaves of plants of the new Guzmania are more arching and broader than leaves of plants of the cultivar 'Festival'.
3. Inflorescences of plants of the new Guzmania are more branched than inflorescences of plants of the cultivar 'Festival'.
4. Sepal color of plants of the new Guzmania is brighter yellow than sepal color of plants of the cultivar 'Festival'.

The accompanying colored photographs illustrate the overall appearance of the new cultivar, showing the colors as true as it is reasonably possible to obtain in colored reproductions of this type.

The first photograph comprises a top perspective view of a typical potted plant of 'Lambada'.

The second photograph comprises a top perspective view of a typical inflorescence of 'Lambada'.

The third photograph comprises a close-up view of a typical flower of 'Lambada'.

Flower and foliage colors in the photographs may differ from the actual colors due to light reflectance.

The new Guzmania has not been observed under all possible environmental conditions. The phenotype may vary somewhat with variations in environment such as temperature and light intensity, without, however, any variance in genotype. The following observations, measurements and comparisons describe plants grown in Erica, The Netherlands, in a glass greenhouse with average day and night temperatures of 21° C., light levels ranging from 3,000 to 3,500 footcandles and exposed to long photoperiods.

In the following description, color reference are made to The Royal Horticultural Society Colour Chart except where general terms of ordinary dictionary significance are used.

Botanical classification: Guzmania cultivar 'Lambada'.

Parentage: Naturally occurring mutation of the non-patented cultivar 'Festival'.

Propagation: By cuttings or by tissue culture.

Plant description:

*Plant shape.*—Upright, inverted triangle, symmetrical.

*Growth habit.*—Erect when young, becoming outwardly arching as leaves develop. Appropriate for 14 to 16-cm containers.

*Plant height.*—About 65 cm from soil level to top of inflorescence.

*Plant vigor.*—Moderately vigorous.

*Crop time.*—About 12 months are usually require from planting of a young plant to a finished 14 to 16-cm container.

*Rooting.*—Tolerant of wet media, but well-drained media is recommended. Time to initiate roots: Summer: About 15 days at 21° C. Winter: About 23 days at 21° C.

*Foliage description.*—Arrangement: Rosette, spiral phyllotaxis. Quantity: 25 to 30. Leaf shape: Linear. Leaf length: 24 to 60 cm. Leaf width: 2 to 4 cm. Margin: Entire. Leaf tip: Apiculate. Leaf texture: Leathery, smooth, glabrous. Leaf color: Adaxial surface: 137B. Abaxial surface: 137C.

Flower description:

*Flower arrangement.*—Terminal inflorescences of 40 to 50 single cup-shaped flowers subtended by bright yellow sepals and bright red floral bracts. At base of floral axis, inflorescence is compound and subtended by showy primary bracts. At top of floral axis, inflorescence consists of single flowers without primary bracts. Plants can be flowered yeararound.

*Flower diameter.*—6 to 8 mm.

*Flower depth (height).*—4 to 6 cm.

*Scape bracts.*—Arrangement: Arranged spirally around the inflorescence main stem. Form: Narrow, very strongly apiculate. Color: Base: Dark red. Center: Dark green. Apex: Dark red.

*Primary bracts.*—Arrangement: At base of floral axis, one per compound inflorescence. Texture: Smooth. Color: 34B.

*Floral bracts.*—Arrangement: Covers about 70% of the length of an opened flower. Texture: Smooth. Color: 41A.

*Sepals.*—Arrangement: Three fused to form a tube. Only about 30% visible, 70% covered by floral bracts. Texture: Smooth. Shape: Elongate, oblong. Margin: Entire. Tip: Obtuse. Size: Length: 4 to 5 mm Width: 3 to 6 mm Color: Adaxial surface: 5B/7C. Abaxial surfaces: 9C.

*Petals.*—Arrangement: Three overlapping forming a cup. Appearance: Shiny, thin, delicate. Texture: Smooth. Shape: Elongate, oblong. Margin: Entire. Tip: Rounded. Size: Length: 4 to 5 mm Width: About 6 mm Color: When opening: 154A. Abaxial and adaxial surfaces: 154A. Fading to: 146B, after senscence, 147A to black.

*Peduncle (at base of compound inflorescences).*—Length: About 1 cm. Color: 41A. Angle: About 70° to the stem.

*Stamens.*—Stamen number: Three with two filaments each. Anther shape: Bi-lobate. Anther size: 4 to 5 mm. Anther color: 152C. Pollen color: Pollen not observed.

*Pistils.*—Pistil number: One. Stigma shape: Three-armed. Stigma color: 141B. Style color: 151D. Style length: About 3.5 mm. Ovary number: 3 fused carpels.

Disease resistance: No known Guzmania diseases observed to date under commercial practice.

Seed production: Seed production has not been observed.

It is claimed:

1. A new and distinct cultivar of Guzmania plant named 'Lambada', as illustrated and described.

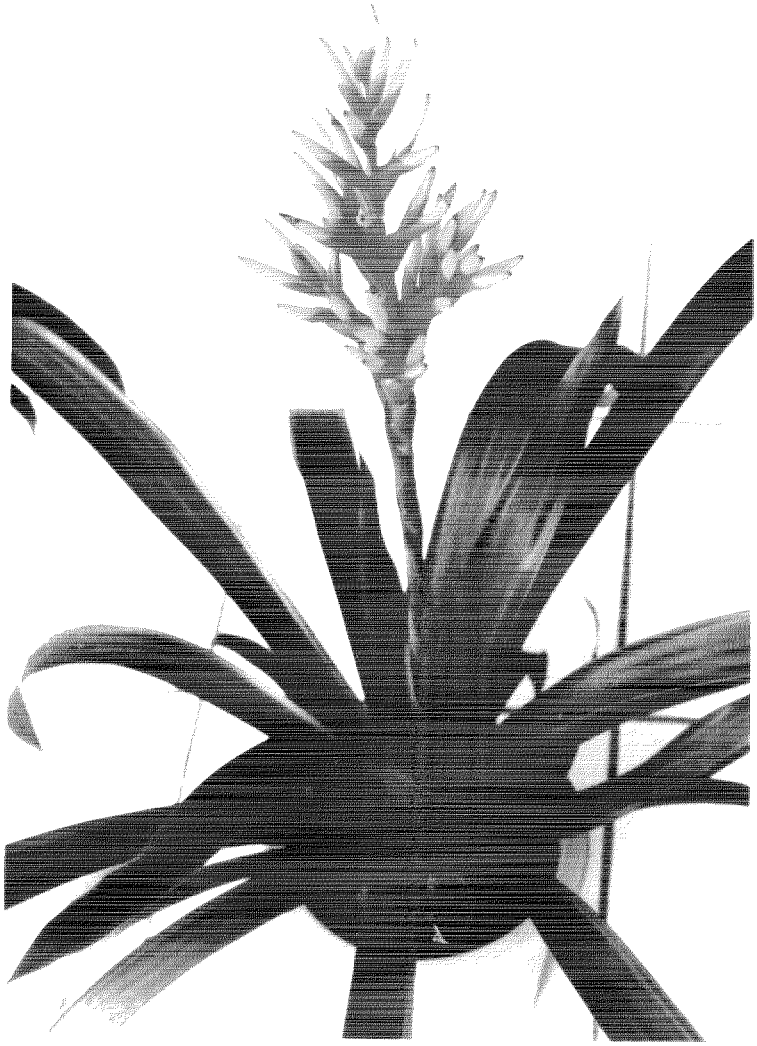

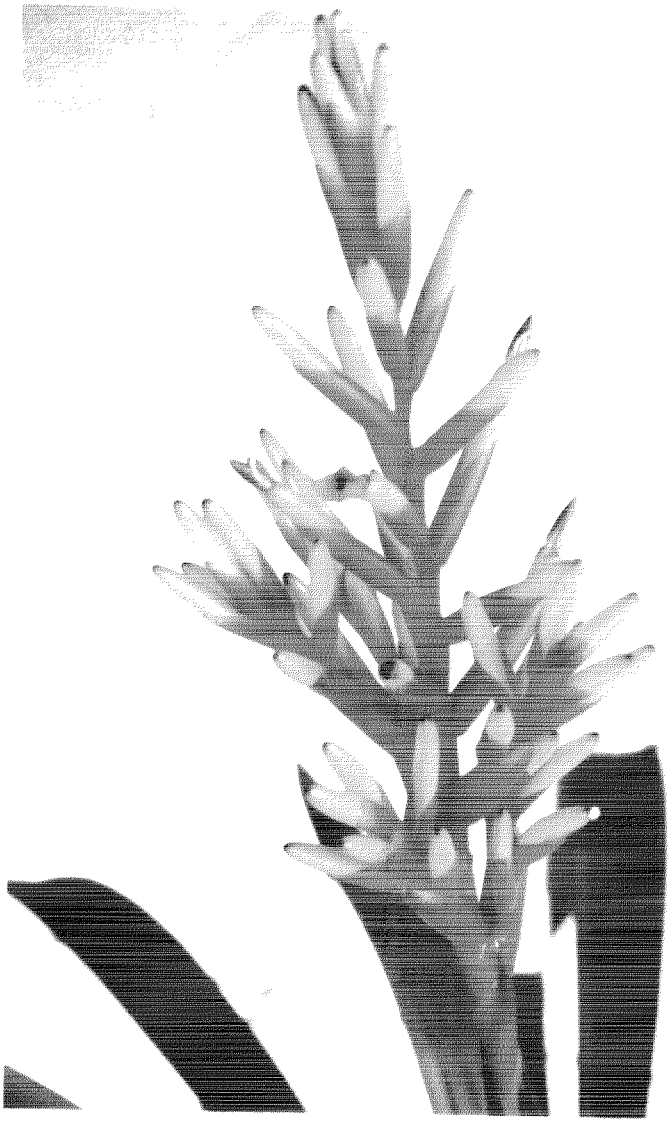

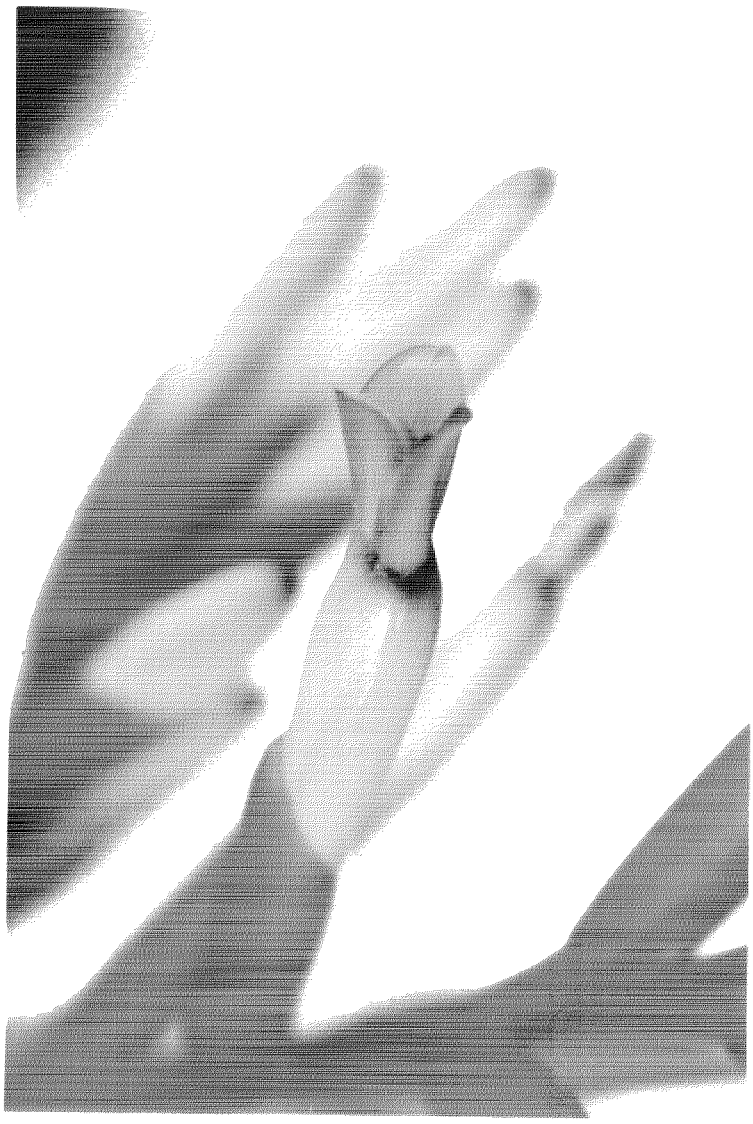

* * * * *